United States Patent [19]

Bucchianeri

[11] 4,424,720
[45] Jan. 10, 1984

[54] MECHANISM FOR SCREW DRIVE AND SYRINGE PLUNGER ENGAGEMENT/DISENGAGEMENT

[75] Inventor: Richard M. Bucchianeri, Escondido, Calif.

[73] Assignee: IVAC Corporation, San Diego, Calif.

[21] Appl. No.: 216,768

[22] Filed: Dec. 15, 1980

[51] Int. Cl.³ .................... F16H 25/20; A61M 5/00
[52] U.S. Cl. ................... 74/89.15; 74/97; 74/424.8 A; 128/DIG. 1; 222/390; 604/155
[58] Field of Search ............... 74/89.15, 97, 424.8 A, 74/424.8 VA; 92/128; 128/DIG. 1, 218 A, 236, 214 F; 222/327, 333, 390; 269/173, 174, 175, 181, 182; 604/155, 152, 208, 211

[56] References Cited

U.S. PATENT DOCUMENTS

| | | | |
|---|---|---|---|
| 1,231,625 | 7/1917 | Lee | 269/182 |
| 1,255,786 | 2/1918 | Phillips | 74/424.8 A |
| 1,393,111 | 10/1921 | Getchell | 74/97 |
| 1,905,569 | 4/1933 | Rapellin | 74/424.8 A |
| 2,345,148 | 3/1944 | Protor | 74/424.8 A |
| 2,498,672 | 2/1950 | Glass | 128/236 |
| 2,612,057 | 9/1952 | Gray et al. | 74/424.8 A |
| 2,627,270 | 2/1953 | Glass | 128/218 A |
| 2,702,547 | 2/1955 | Glass | 128/218 A |
| 2,779,366 | 1/1957 | McKenzie | 269/182 |
| 3,701,350 | 10/1972 | Guenther | 128/DIG. 1 |
| 3,858,581 | 1/1975 | Kamen | 128/218 A |
| 4,189,950 | 2/1980 | Killian | 74/424.8 A |
| 4,191,187 | 3/1980 | Wright | 128/218 A |

FOREIGN PATENT DOCUMENTS

| | | | |
|---|---|---|---|
| 455095 | 1/1928 | Fed. Rep. of Germany | 74/97 |
| 550749 | 3/1923 | France | 222/390 |
| 380803 | 9/1964 | Switzerland | 74/97 |
| 4518 | of 1913 | United Kingdom | 269/174 |

Primary Examiner—Lawrence J. Staab
Attorney, Agent, or Firm—Fulwider, Patton, Rieber, Lee & Utecht

[57] ABSTRACT

A mechanism for screw drive and syringe plunger engagement and disengagement for a syringe infusion pump, wherein a split-nut pair are moveable into and out of engagement with a lead screw by means of rotary cam control, the rotary cam being keyed with a crank disk that is coupled to a crank arm, which operates as the syringe plunger mover. The crank arm is rotatable into and out of engagement with the syringe plunger, such rotation also causing the split-nut pair to move into and out of engagement with the lead screw. Index and cam means are carried by the crank arm to aid in proper alignment with the syringe plunger, and a sensor is provided for monitoring proper engagement of the crank arm with the plunger.

51 Claims, 18 Drawing Figures

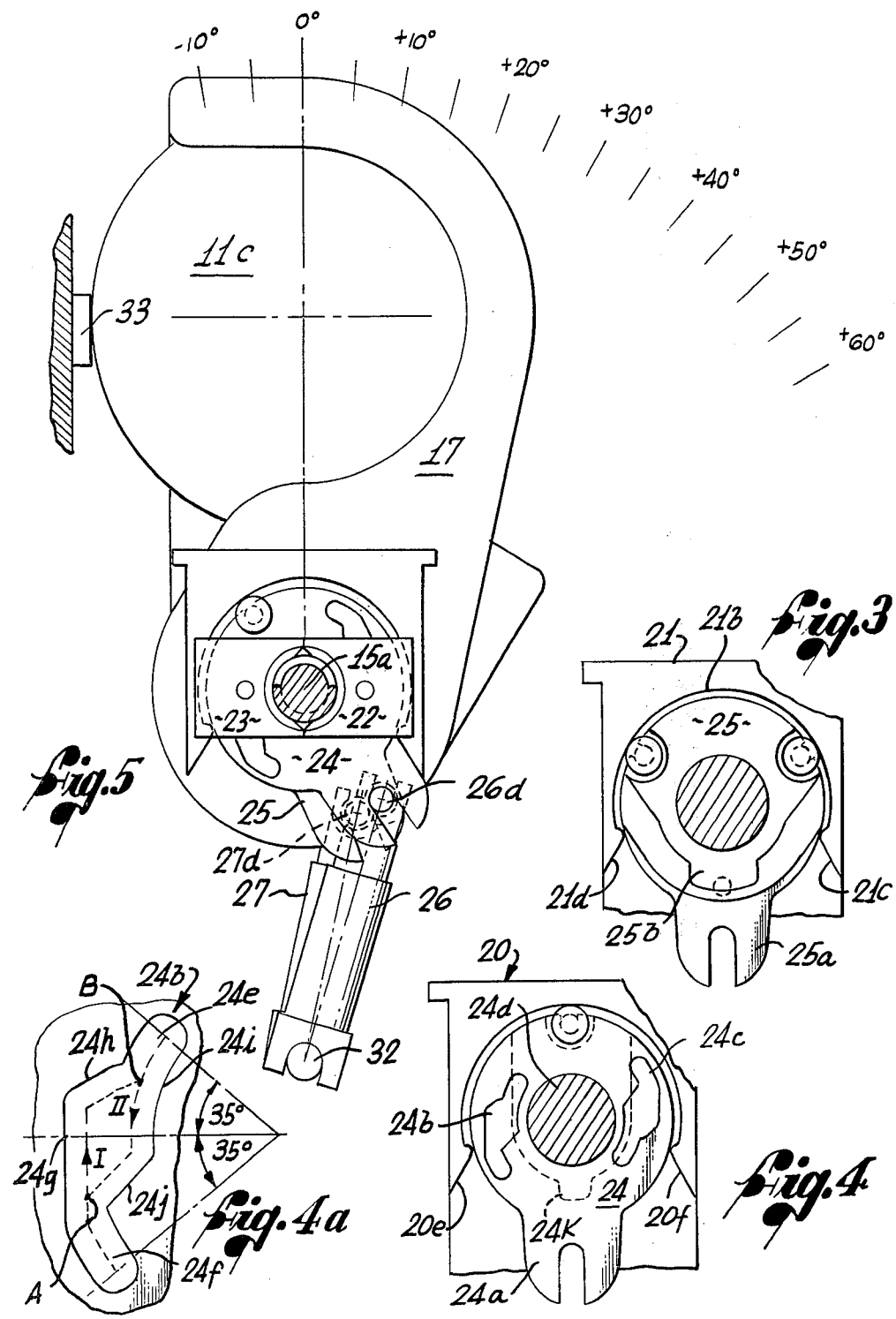

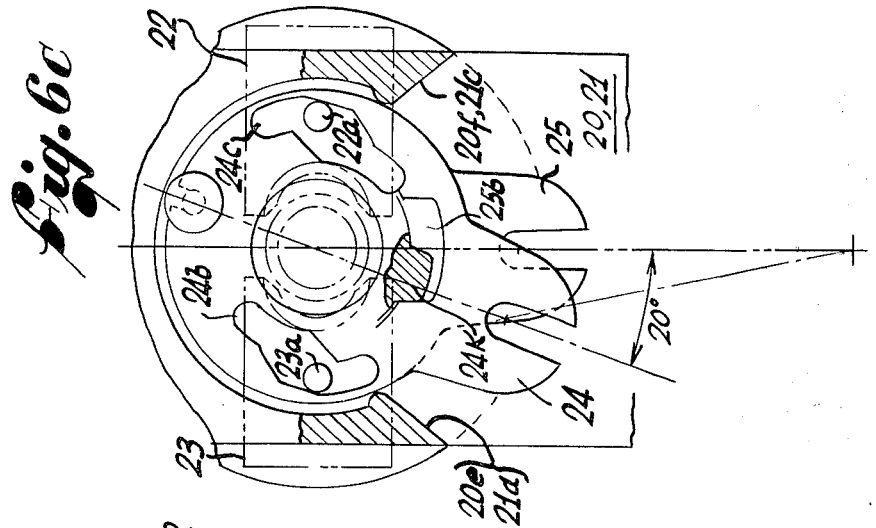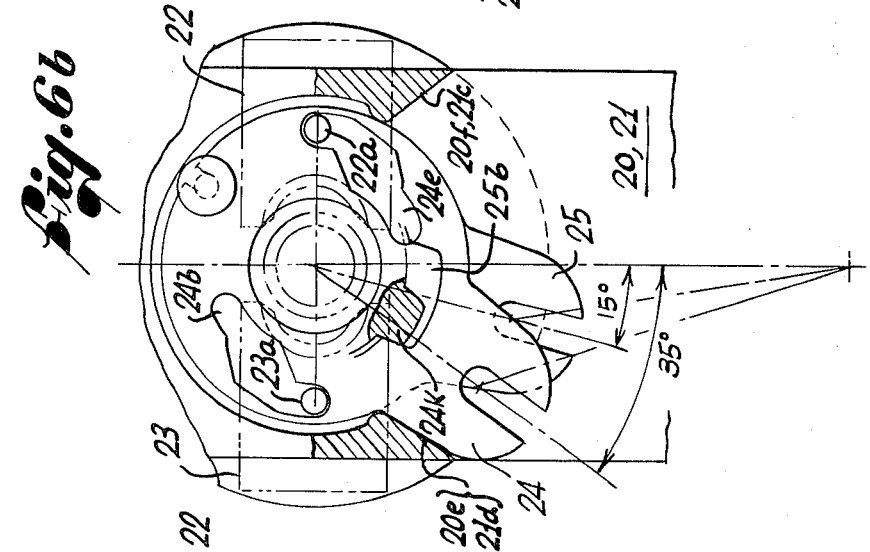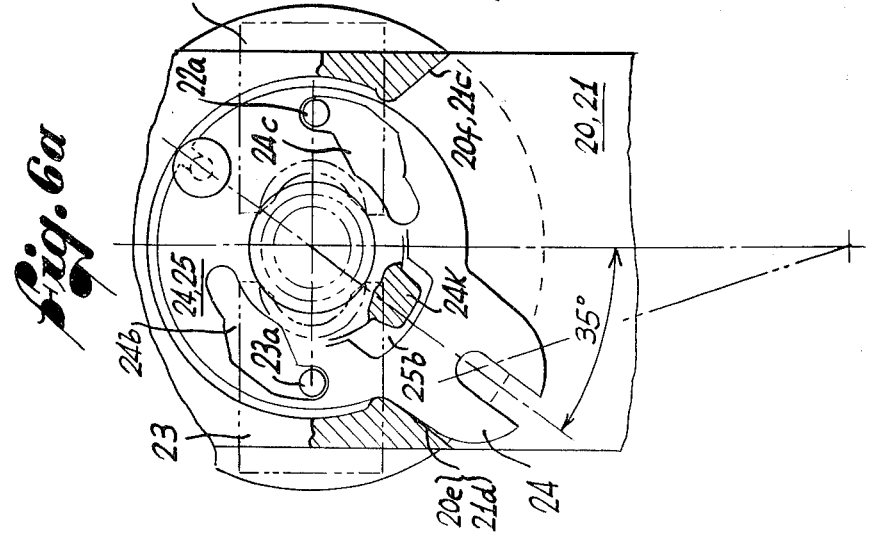

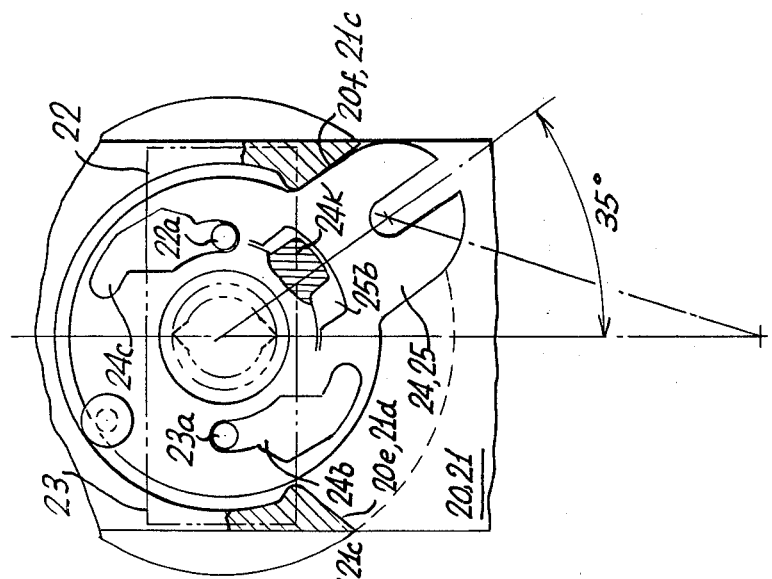
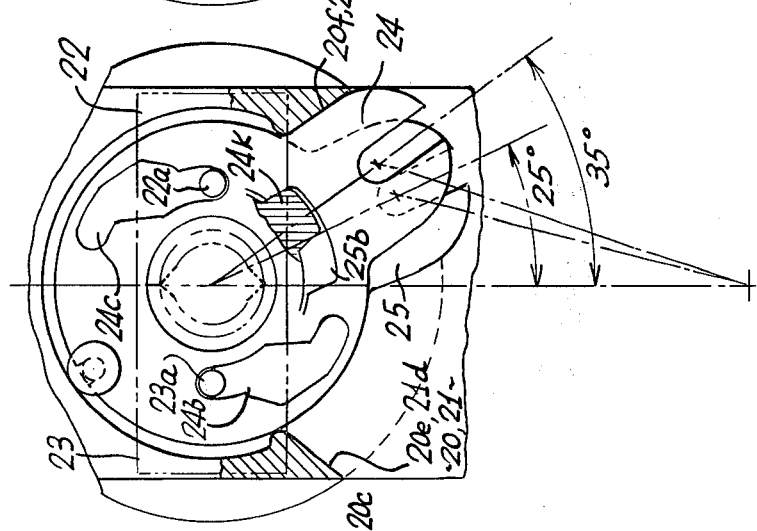
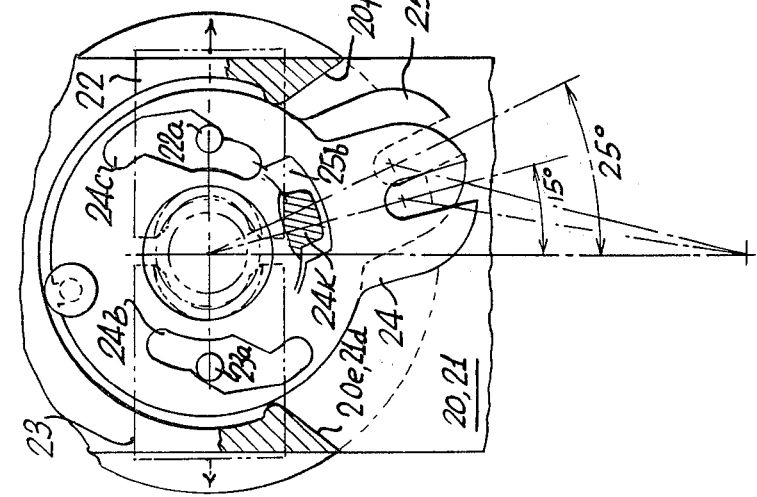

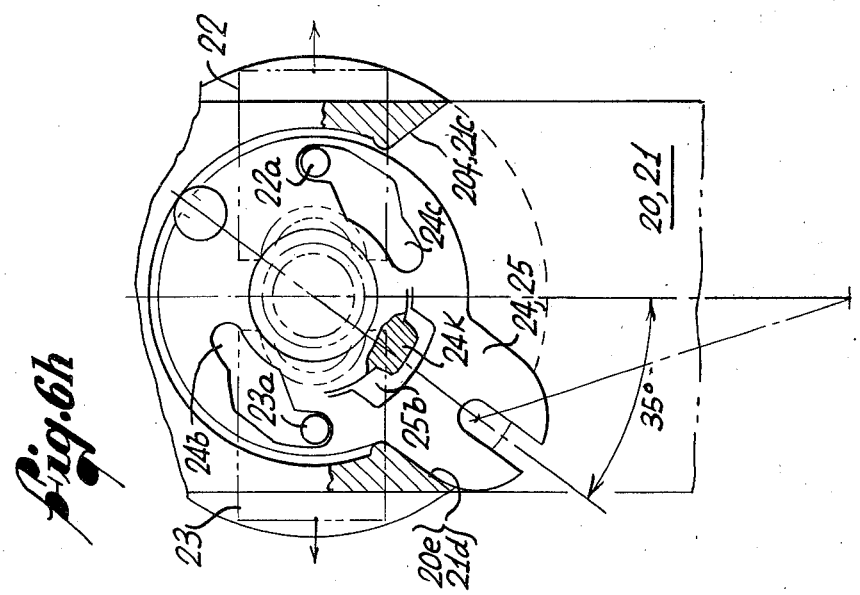
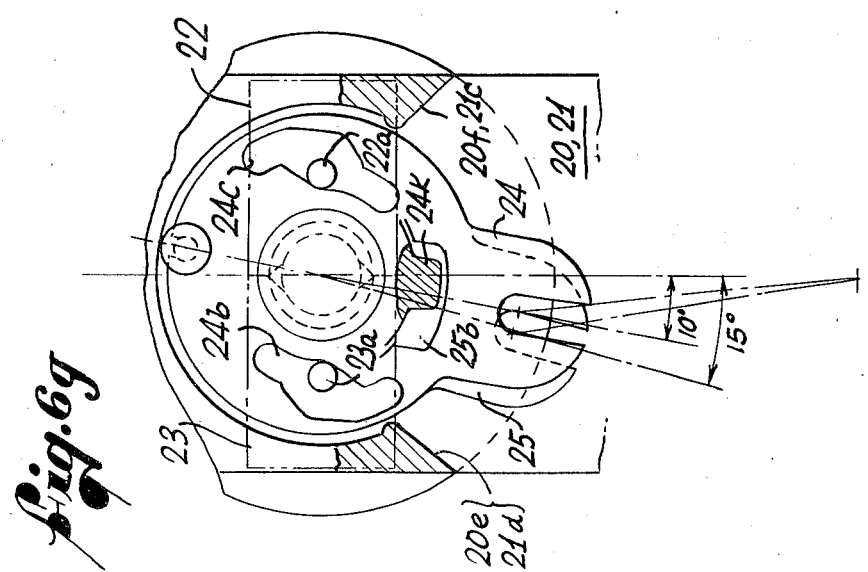

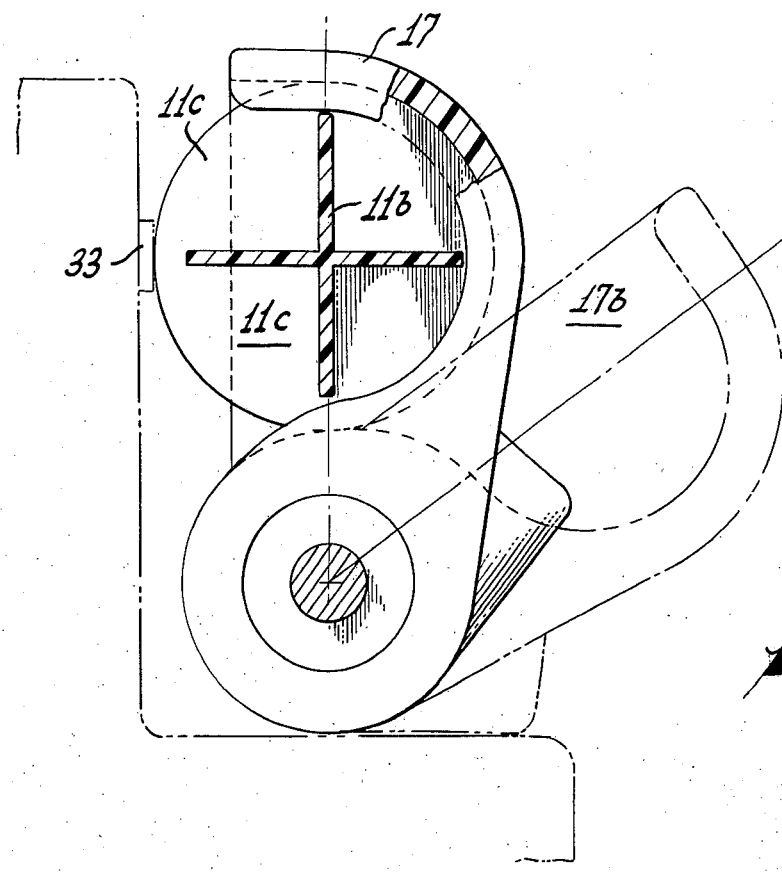
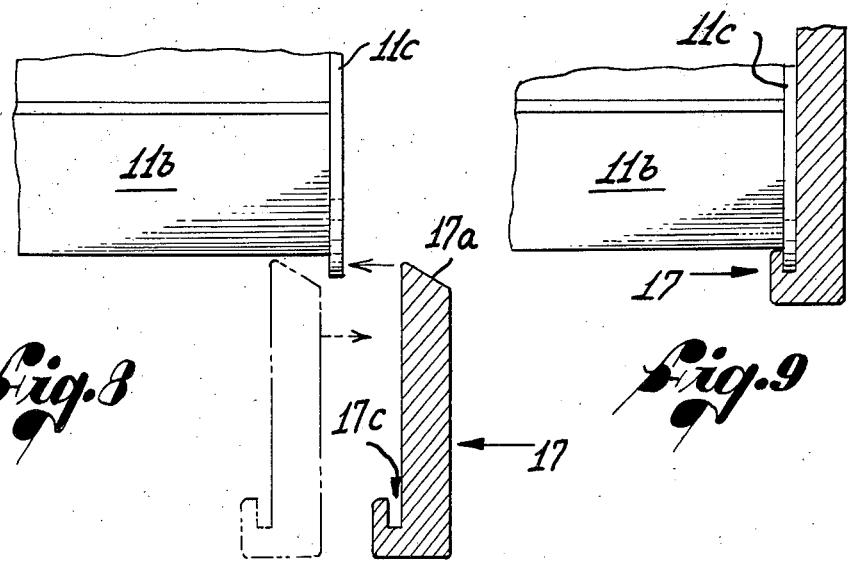

MECHANISM FOR SCREW DRIVE AND SYRINGE PLUNGER ENGAGEMENT/DISENGAGEMENT

BACKGROUND OF THE INVENTION

This invention relates generally to improvements in mechanisms for screw drive engagement and disengagement, and more particularly, to a new and improved mechanical system for use in a syringe pump of the type requiring engagement and disengagement of a lead screw to facilitate installation of a syringe for parenteral administration (referred to herein as "intravenous administration" or "IV administration") of medical fluids.

The usual medical procedure for the gradual IV administration of fluids into the human body, such as fluid replacement, liquid nutrients, blood or plasma, makes use of apparatus which is commonly referred to in the medical arts as an intravenous solution administration set. Such a set typically is a disposable plastic product, and comprises a drop chamber adapted to be connected to a fluid source, a length of tubing extending from the chamber to the patient and a valve mechanism, such as a roller clamp on the tubing.

The drip chamber of the IV administration set serves a dual function of allowing a nurse or other attendant to observe the rate at which the fluid drips out of the fluid source and also creates a reservoir for the fluid at the lower end of the drip chamber to insure that no air enters the main feeding tube leading to the patient.

While observation of the rate of drop flow via the drop chamber is a simple way of controlling the amount of fluid fed to a patient over a period of time, its ultimate effectiveness requires that a relatively constant vigil be maintained on the drop flow, lest it cease entirely due to exhaustion of the fluid supply or vary unacceptably from the set rate.

In addition to the aforedescribed difficulties, the IV administration of medical fluids by gravity induced hydrostatic pressure infusion of the liquid from a fluid source suspended above a patient, may be susceptible to fluid flow rate variations due to changes in the fluid level in the bottle, changes in temperature, changes in the venous or arterial pressure of the patient, patient movement, and drift in the effective setting of the roller clamp or other valve mechanism pinching the feeding tube. Moreover, there are a number of situations, such as in intensive care, cardiac and pediatric patients, or where rather critical drugs are being administered, where the desired drop flow rate must be capable of rather precise selection and must not drift beyond certain prescribed limits in spite of varying load conditions.

In view of the foregoing, a number of electrical monitoring systems, drop flow controllers and infusion pumps have been developed in recent years to infuse medical fluids into patients at precisely regulated fluid flow rates. In particular, syringe pumps have been developed and have become popular in the IV administration of fluids into the human body, such syringe pumps typically embodying a motor driving a plunger within a syringe body to expel fluid from the syringe at a controlled rate through a length of tubing and into the patient.

One specific variety of syringe pump has a syringe plunger mover that is coupled for engagement with a rotary-driven lead screw for linear travel along the lead screw. These pumps are especially adapted to receive a self-contained syringe, installed to have the syringe plunger mover drive the syringe plunger. Because such syringes are typically pre-loaded with varying amounts of fluid and the syringe plunger mover may be in any position along its linear travel from a previous use, some mechanism is necessarily provided for selectively disengaging the syringe plunger mover from the lead screw to enable manual repositioning of it into alignment with the free end of the syringe plunger upon installation.

In the past, such syringe pumps have commonly used a spring-biased mechanism that required continuous actuation of a button or lever in order to maintain the syringe plunger mover in a state of disengagement from the lead screw while the mover was repositioned. Premature release of such a button or lever while attempting to reposition the syringe plunger mover, as was prone to happen, however, caused damage to the lead screw and to the nut or other component coupling the mover to the lead screw due to thread scraping, and otherwise rendered difficult the process of alignment. Also, the spring-biasing of these mechanisms created substantial thread collision forces upon re-engagement of the lead screw, particularly in instances of thread misalignment, tending to cause further excess wear and damage to the instrument.

Another common feature of existing syringe pumps has been "unbalanced" engagement with the lead screw, e.g., as by utilization of a half-nut coupled to the syringe plunger mover and threadedly engaged on just one side of the lead screw. To maintain engagement, substantial force must be exerted by the half-nut or its equivalent on the lead screw, which results in relatively great friction and bowing of the lead screw. At least one solution to this latter problem has been known, but it involves use of a complex and relatively expensive collet-type collapsible nut.

In many of these pumps, moreover, syringe installation has been made even more difficult by the requirement that the mover be properly aligned before the syringe is installed. This necessitates a time consuming trial-and-error procedure in which the syringe is held out of the way, at least partly above or to one side of the pump, with one hand, while the spring-biased disengagement button or lever is actuated and the mover is repositioned, all with the other hand. An attempt is then made to install the syringe, but if there is misalignment, the procedure must be repeated.

Hence, those concerned with the development and use of mechanical drive systems of the type suitable for use in IV fluid administration systems, and particularly those concerned with the design of IV syringe pumps, have long recognized the need for an improved, relatively simple, economical, durable and reliable mechanism for engagement and disengagement with a lead screw that also provides for convenient installation of a syringe with respect to a syringe plunger mover, in order to obviate the aforedescribed difficulties. The present invention clearly fulfills this need.

SUMMARY OF THE INVENTION

Briefly, and in general terms, the present invention resides in a new and improved mechanism for lead screw engagement and disengagement, in which a traveler mechanism, by means of selective actuation, is moved into and out of threaded engagement with the lead screw in a manner virtually eliminating the possibility of partial thread engagement that could result in thread scraping, minimizing thread collision forces and ensuring proper thread alignment before forcing the traveler mechanism into lead screw engagement.

With specific reference to syringe pumps of the aforementioned type, the invention additionally resides in a syringe plunger mover mounted for rotation between positions of engagement and disengagement with the free end of a syringe plunger. The mover arm in the disengaged position allows for unobstructed syringe installation regardless of the linear position of the mover with respect to the plunger, and also is capable of sliding movement into proper alignment from either side of the free end of the installed plunger.

Moreover, in a further aspect of the invention, the mover serves as part of a rotary crank means for actuating the traveler mechanism whereby rotation of the mover to its disengaged position with the syringe plunger causes traveler mechanism disengagement with the lead screw, and conversely, rotation of the mover into engagement with the plunger causes traveler mechanism engagement with the lead screw.

The traveler mechanism includes a biasing system for releasably biasing it in either the state of engagement or the state of disengagement with the lead screw, the biasing system preferably producing an over-center action as the traveler mechanism moves between those two states. In an important aspect of he invention, the traveler mechanism does not move into or out of engagement with the lead screw until after its biasing system has travelled over center, and because of the manner in which the traveler mechanism is coupled to its actuator, the traveler mechanism then completes its movement independent of the actuator. Thus after initial external actuation, the traveler mechanism completes engagement or disengagement, as the case may be, due only to its own internal biasing system, with means provided to limit collision forces with the lead screw upon engagement and to cause rapid disengagement once the biasing system is over center.

More particularly, the present invention provides a new and improved mechanism in which a split nut-pair are mounted for movement into and out of engagement with the lead screw, each split nut having a projecting pin received in a cam groove formed in a rotary cam disk so that rotation of the cam disk controls movement of the split nuts. The split-nut pair is moved and locked into lead screw engagement by rotation of the cam disk in one direction to the fullest possible extent, while movement of the cam disk to the fullest extent possible in the opposite direction moves and locks the split-nut pair out of engagement, mechanical limits or stops being provided to limit rotational travel of the cam disk. Biasing means in the form of a compression spring assembly is connected to the cam disk for over-center action, and an actuator mechanism is provided for bringing the spring-to-cam disk assembly from one or the other of its extreme rotational positions over center towards the opposite extreme position, at which point the spring assembly provides automatic rotational control of cam disk movement to the opposite extreme. In this regard, the actuator mechanism in not fixedly coupled to the cam disk, but rather is loosely keyed so that after bringing the cam disk over center, the cam disk releases from the actuator mechanism and continues to move to the opposite extreme position due solely to the biasing effect of its own spring system. Mechanical limits or stops for the actuator mechanism are provided to help protect the split-nut pair and lead screw against damage due to overly vigorous operation of the actuator mechanism by the user, particularly during engagement.

The cam disk grooves each include a pair of arcuate locking portions for retaining the split-nut pins in the fully disengaged position or the fully engaged position, depending on the rotational state of the cam disk, and further include separate segments between these two locking portions for prescribed control of the split-nut pair during engagement and rapid separation of the split-nut pair during disengagement. Each of these latter segments is configured within the cam grooves so that very little, if any, split-nut pair movement occurs until after the spring-to-cam disk assembly passes over center during rotation. The cam groove segment controlling split-nut pair engagement is configured to limit the collision force between the threads of the split-nut pair and the threads of the lead screw.

Again, with reference to the syringe pump for which the aforedescribed lead screw engagement and disengagement mechanism was specifically developed, the actuator mechanism comprises a crank arm having a one end connected to a crank shaft, which in turn connects to a crank disk for keying to the cam disk. The crank arm is rotatable between closed and opened positions whereby its free end either grasps or releases, respectively, the free end (or "thumb-rest") of a syringe plunger. Another compression spring assembly is connected to the crank disk for over center action tending to lock the crank arm in one or the other of its extreme rotational states. The opened position of the crank arm corresponds to disengagement of the split-nut pair from the lead screw, and, conversely, the crank arm closed position corresponds to split-nut pair engagement with the lead screw. Importantly, the respective spring assemblies for the crank disk and the cam disk automatically lock them in the open-and-disengaged states during manual positioning of the crank arm into alignment with the thumbrest of the syringe plunger.

As previously mentioned, opening the crank arm provides clearance for installation of a syringe regardless of the linear position of the crank arm at the time. In particular, the crank arm may initially be linearly positioned forwardly of the thumbrest, it being possible with the present invention to then slide the crank arm rearwardly past the thumbrest and then forwardly into alignment for crank arm closure. In this regard, the crank arm has a beveled edge that lifts the thumbrest out of the way to permit the crank arm to pass by from the forward (i.e., syringe plunger) side of the thumbrest. For automatic crank arm alignment when approaching the thumbrest from the rearward side, the margin of the crank arm pushing surface catches the lip of the thumbrest as a manual indication of alignment, from which crank arm rotation to the closed position follows.

A fixed light source and photoelectric sensor arrangement provides a reference light beam which is interrupted by an opaque flag in all rotational positions of the crank arm, except when the crank arm is closed and properly grasping the thumbrest, so that a signal can be developed to enable proper pump function.

The new and improved lead screw and syringe plunger engagement/disengagement mechanism of the present invention is extremely simple and reliable. The mechanism provides proper balanced-force engagement of the lead screw, and locked disengagement of the split-nut pair to eliminate the need for continuous actuation of a button or lever by the user in order to manually position the crank arm for alignment with the plunger thumbrest. The mechanism also provides for convenient installation of a syringe that does not require pre-alignment of the crank arm.

The above and other objects and advantages of the present invention will become apparent from the following more detailed description, when taken in conjunction with the accompanying drawings of an illustrative embodiment.

BRIEF DESCRIPTION OF THE DRAWINGS

FIG. 2 is an exploded perspective view of the structural components of the mechanical engagement and disengagement system, while

FIG. 3 is a fragmentary elevational view of the crank disk and rear housing taken from the side opposite that shown in FIG. 2;

FIG. 4 is a elevational view of the cam disk taken from the side opposite that shown in FIG. 2, and showing a fragmented outline of the front housing around the cam disk, while FIG. 4a is a enlarged, fragmentary view of one of the cam grooves formed in the cam disk;

FIG. 5 is a view, primarily schematic in nature, taken along the axis of the lead screw from the left of the split-nut pair as shown in FIG. 2, and illustrates the interrelationship between the primary components of the mechanical engagement and disengagement system of the invention;

FIG. 6a–6h is a series of fragmentary views, also primarily schematic in nature, in which the the split-nut pair and pins, the cam grooves and the key of the cam disk, and the keyway of the crank disk are superimposed and shown in a variety of positions relative to one another;

FIG. 7 is a fragmentary sectional view taken along the line 7—7 in FIG. 1, and partially broken away to show the manner in which the crank arm grasps the thumbrest of the syringe plunger, the fully opened position of the crank arm being shown in phantom;

FIG. 8 is a fragmentary top plan view, primarily schematic in nature and partially in section, illustrating linear travel of the crank arm, in the fully opened position, into alignment with the thumbrest; and FIG. 9 is a view similar to FIG. 8, showing the crank arm rotated to the fully closed position, grasping the thumbrest.

DESCRIPTION OF THE PREFERRED EMBODIMENT

Figure 1:
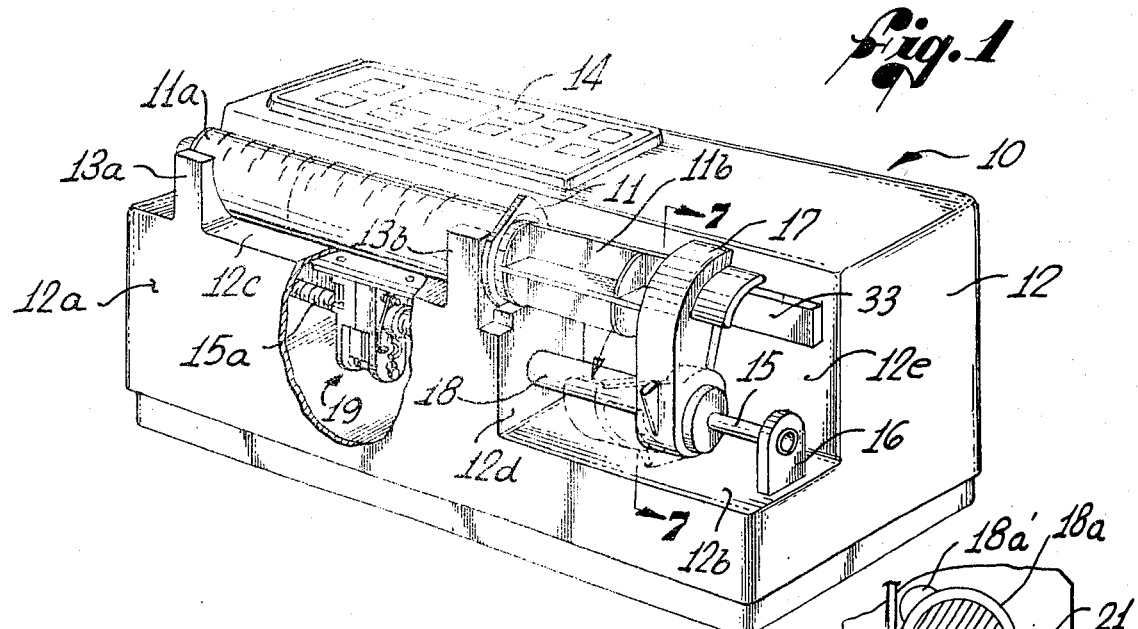
FIG. 1 is a perspective view, partially broken away, illustrating a syringe infusion pump utilizing a mechanical engagement and disengagement system embodying the principles of the present invention.

Referring now to the drawings for the purpose of illustrating the presently preferred embodiment of the new and improved mechanical engagement/disengagement system of the present invention, and particularly to FIG. 1 thereof, there is shown a syringe infusion pump, indicated generally by reference numeral 10, in which the mechanical system is embodied. Although reference is made to the intravenous administration environment, and particularly to syringe pumps, for which the unique mechanical engagement/disengagement system of the present invention was specifically developed, it is to be understood that this is by way of example only, and the system as set forth in the ensuing description is suitable for use in other environments and for a wide variety of applications other than intravenous administration.

The infusion pump 10 shown in FIG. 1 has a syringe 11, comprising a body 11a and a plunger 11b, installed in it to be acted upon by the mechanical system embodied in the pump for the controlled delivery of fluid from the syringe through an IV tube (not shown) to the patient. The syringe 11 is of the self-contained variety (i.e., when installed it is pre-loaded with the precise volume of fluid to be infused to the patient) and the fluid is delivered by means of a single, prolonged pump stroke applied by the pump 10 to the syringe plunger 11b. Typically, in use the syringe 11 does not draw fluid from another source, as by cycling the syringe through alternate fill and pump strokes.

The syringe pump 10 is contained in a generally oblong housing 12 including, along one side of the housing, a compartment 12a, in which various elements of the mechanical system of the present invention are disposed, and a base surface 12b adjacent to and generally lower than the compartment. Formed on an upper surface 12c of the compartment 12a are a pair of longitudinally spaced-apart, upstanding cradle members 13a, 13b into which the cylindrical body 11a of the syringe 11 is installed, with the syringe plunger 11b extending out over the base surface 12b. Laterally adjacent to the compartment 12a and the base surface 12b, on the main housing 12 of the syringe pump, there is shown a control panel 14 including various operating controls and indicators, which need not be described further herein for an understanding of the invention.

A traveler rod 15 extends almost the length of the syringe pump, through an end wall 12d of the compartment 12a at its intersection with the base surface 12b, so that a portion of the traveler rod is disposed within the compartment and the remaining portion of the traveler rod extends above and across the base surface. The traveler rod portion within the compartment 12a defines a lead screw 15a, while the portion outside the housing presents a smooth cylindrical surface. One end of the traveler rod 15 is supported by, and journalled for rotation in, an upstanding end bracket 16 protruding from the base surface 12b, and the other end is coupled to a geared motor (not shown), mounted within the compartment 12a for selective rotation of the traveler rod under the control of any appropriate electrical control system. One suitable control system is shown and described in an application for U.S. Pat., Ser. No. 216,762, filed concurrently herewith, entitled "Motor Control System", inventor Wilber H. Bailey et al.

In accordance with the invention, the thumbrest 11c at the free end of the syringe plunger 11b is grasped by one end of a syringe plunger mover, which will be referred to herein as the crank arm 17. The thumbrest 11c is obscured in FIG. 1 by the crank arm 17, but is clearly shown in FIGS. 7–9. The crank arm 17 has its other end fixedly attached to a hollow crank shaft 18, which is received over the traveler rod 15. The relationship between the crank shaft 18 and the traveler rod 15 is such that not only are they rotatable relative to one another, but the crank shaft is also capable of linear travel along the traveler rod. Like the traveler rod 15, the crank shaft 18 extends through the compartment end wall 12d and into the compartment 12a where the crank shaft is coupled to a traveler mechanism, indicated generally by reference numeral 19, received around the lead screw 15a. The traveler mechanism 19 can be seen in FIG. 1 through the portion of the compartment 12a that has been broken away for clarity.

As shown in FIG. 1, the crank arm 17 is manually rotatable about the traveler rod 15 between a so-called "closed" position, in which the crank arm grasps the thumbrest 11c of the syringe plunger 11b, and a so called "opened" position (shown in phantom), in which the crank arm is rotated down and away for release from the thumbrest. By means described in some detail below, rotation of the crank arm 17 between the closed and opened positions actuates the traveler mechanism 19 between states of engagement and disengagement with the lead screw 15a, respectively.

When the traveler mechanism 19 is engaged with the lead screw 15a, rotation of the lead screw causes the traveler mechanism, and therefore the crank shaft 18 and the crank arm 17 as well, to travel forwardly along the traveler rod (or towards the left in FIG. 1) at a rate determined by the rate of rotation and the pitch of the lead screw. The free end of the crank arm 17 in turn pushes the plunger 11b forwardly into the syringe body 11a, exerting positive pressure on the fluid contained therein and causing it to be delivered through the IV tube to the patient.

Conversely, when the traveler mechanism 19 is disengaged from the lead screw 15a, the entire assembly consisting of the crank arm 17, the crank shaft 18 and the traveler mechanism 19 can be manually moved freely along the traveler rod 15 so as to position the crank arm into alignment with the thumbrest 11c prior to rotating it into the closed position.

Figure 2A:
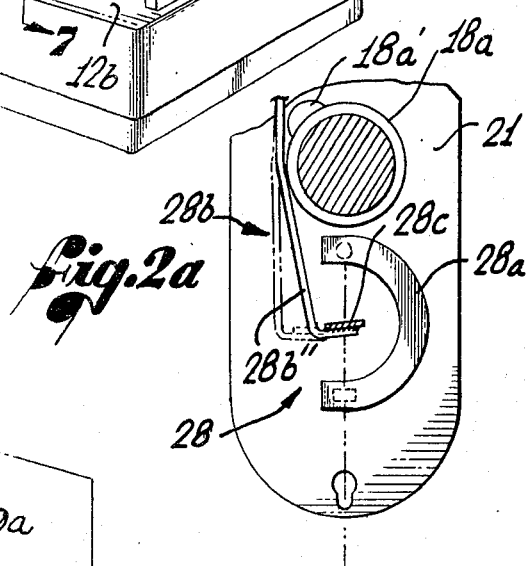
FIG. 2a is a fragmentary side elevational view of the optical mechanism for monitoring proper engagement of the crank arm with the thumbrest at the free end of the syringe plunger.
Figure 2:
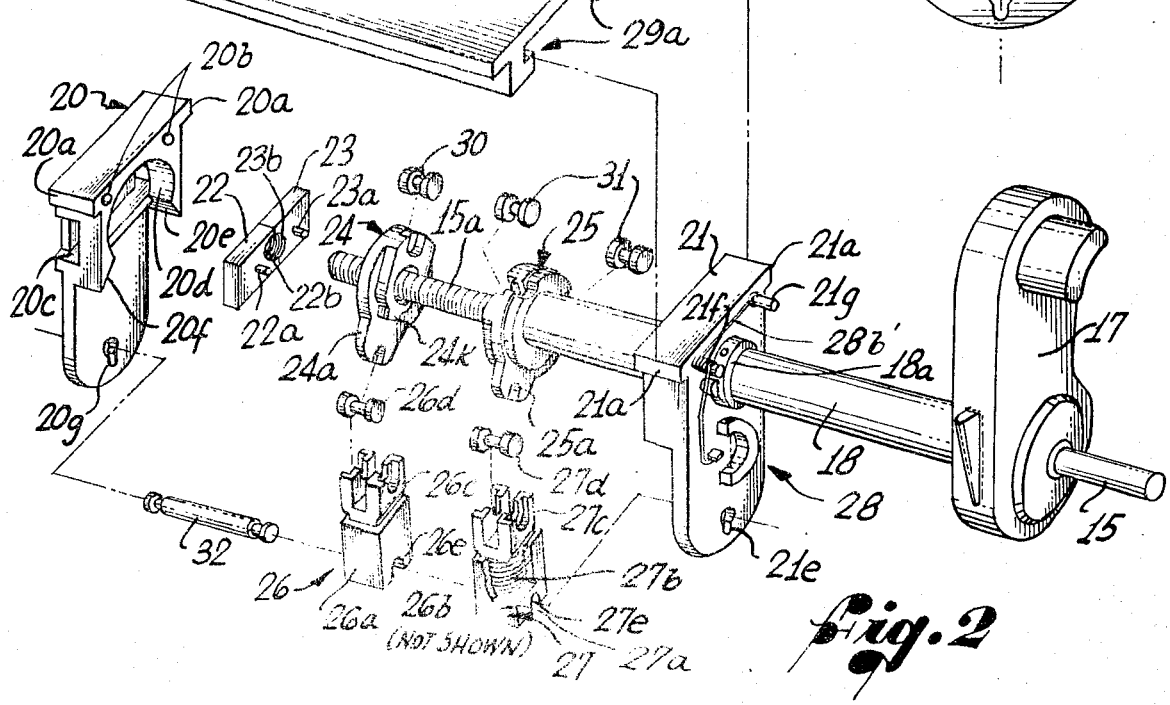

The component parts of the traveler mechanism 19 are shown exploded apart in FIG. 2 so that their relationship to each other can be more readily appreciated. The traveler mechanism 19 is split into a front housing 20 and a rear housing 21, and primarily comprises a split-nut pair 22, 23, a cam disk 24, a crank disk 25 and two spring assemblies 26, 27. Mounted on the outside surface of the rear housing 21, facing towards the crank arm 17, is an optical mechanism, generally indicated by reference numeral 28, for sensing whether the crank arm is in its closed position and properly grasping the thumbrest 11c.

In assembly, the front housing 20 and the rear housing 21 fasten together through holes 20b, as by screws (not shown). The upper ends of the front housing 20 and the rear housing 21 each have a pair of laterally extending flanges 20a, 21a, respectively, receivable within an extruded channel 29a formed along the bottom surface of a support member 29. The support member 29 fastens to the inside upper surface of the compartment 12a, and the channel 29a forms a guide for the linear movement of the traveler mechanism 19 and holds it against rotation around the axis of the lead screw 15a.

On the inside of the front housing 20, there is formed a slide groove 20c with a centered clearance hole for the lead screw 15a to pass through. The slide groove 20c receives the split-nut pair 22, 23 and acts to guide movement of the split-nut pair radially inwardly or outwardly for threaded engagement or disengagement, respectively, with the lead screw 15a. An enlarged counterbore 20d is also formed in the inside surface of the front housing 20 and functions as a receptacle in which the cam disk 24 rotates, the cam disk being fitted with a disk roller 30 to reduce friction and eccentric rotation of the cam disk.

As best shown in FIG. 4, the counterbore 20d is open at the bottom to receive a downwardly extending wing 24a formed on the cam disk 24. At the counterbore opening, the wall defining the counterbore flares outwardly on each side to define mechanical stops 20e, 20f limiting rotational movement of the cam disk 24 about the lead screw 15a to about 70° in the example of the preferred embodiment. A side of the cam disk wing 24a abuts one or the other of these stops 20e, 20f when the cam disk is rotated clockwise or counter-clockwise, as the case may be, to the maximum extent.

The rear housing 21 (FIG. 3) also has an inwardly facing counterbore 21b in which the crank disk 25 is received for rotation, and a clearance hole concentric with the counterbore 21b through which the hollow crank shaft 18 extends. The rear housing counterbore 21b is similarly open at the bottom to receive a like downwardly extending wing 25a formed on the crank disk 25 and the counterbore wall flares outwardly on each side in the same manner as on the front housing 20 to define mechanical stops 21c, 21d limiting the maximum rotational movement of the crank disk also to about 70°. The crank disk 25 is fitted with two disk rollers 31.

Referring again to FIG. 4, the side of the cam disk 24 facing towards the split-nut pair 22, 23 has formed in it a pair of cam grooves 24b, 24c on diametrically opposite sides of a centered clearance hole 24d for the lead screw 15a. The split-nut pair 22, 23 each have an axially extending pin 22a, 23a received within its corresponding cam groove 24b, 24c for camming control of split-nut pair movement within the slide groove 20c of the front housing 20. The shape of each cam groove is mirrored by the other cam groove exactly 180 degrees opposite itself on the cam disk 24. In other words, corresponding points along each cam groove 24b, 24c can be found diametrically across the center of the cam disk 24.

An enlarged view of one of the cam grooves 24b, is shown in FIG. 4a. The cam groove 24b includes a pair of arcuate locking portions at the rotationally opposite ends of the groove. The radially innermost locking portion (or uppermost groove in FIG. 4a) serves to retain the split-nut pin 23a so that the split nut 23 is locked in the fully engaged position, and therefore will be referred to as the engagement-locking portion 24e of the cam groove 24b. The radially outermost locking portion (or lowermost groove in FIG. 4a) serves a similar purpose for the fully disengaged position of the split nut 23, and will be referred to as the disengagement-locking portion 24f of the cam groove 24b.

Between point A shown in FIG. 4a, at the mouth of the disengagement-locking portion 24f, and point B, at the mouth of the engagement-locking portion 24e, the split-nut pin 23a in effect will trace one of two paths in the cam groove 24b depending on point of origin or, in other words, on the direction of rotation of the cam disk 24. The path I traced during counterclockwise rotation of the cam disk 24 is the radially outermost path indicated by the upwardly directed arrow in FIG. 4a. This corresponds to movement of the split nut 23 from disengagement towards engagement with the lead screw 15a. The cam groove along this engagement path I comprises two segments, a first segment 24g that produces minimal split nut motion, followed by a second segment 24h that causes most of the radially-inwardly directed motion of the split nut 23. The first segment 24g has the purpose of ensuring that the split nut 23 will freely move, i.e., that it is not stuck in the slide groove 20c, and the second segment 24h is configured so as to impact with the split nut pin 23a, tending to reduce the acceleration of the cam disk 24 and, as a result, reducing the collision force between the threads of the split nut 23 and the threads of the lead screw 15a.

The path II traced during clockwise rotation of the cam disk 24 is the radially innermost path indicated by the downwardly directed arrow in FIG. 4a, corresponding to radially outward movement of the split nut 23 from engagement with the lead screw 15a to disengagement. The cam groove along this disengagement path II likewise comprises two segments, a first segment 24i that is a pure arc producing no split nut movement, and a second segment 24j that is steeply ramped to rapidly move the split nut 23 out of engagement with the lead screw 15a.

The opposite side of the cam disk 24 has an axially protruding key 24k (FIGS. 2 and 4) which is receivable in a recessed keyway 25b (FIG. 3) formed in the side of the crank disk 25 that faces the cam disk 24. The cam disk 24 and the crank disk 25 are coupled by means of the key 24k and the keyway 25b, so that rotation of the crank disk 25 controls rotation of the cam disk 24. The cam disk key 24k is loosely fitted in the crank disk keyway 25b in order to allow some independent motion of the cam disk 24 and the crank disk 25 relative to one another. In the preferred embodiment, the total available angular rotation between the key 24k and the keyway 25b is 30°. This independent rotation is primarily required by the cam disk 24 during split-nut engagement, which occurs after the crank disk 25 has brought the spring-to-cam disk system (see below) over center. It also provides for rapid snap-action disengagement of the split-nut pair 22, 23 from the lead screw 15a, as well as allowing the crank arm 17 to rotate all the way to the rub strip 33 if it misses the thumbrest 11c.

A main pivot pin 32 extends in the axial direction between the front housing 20 and the rear housing 21 and mounts at its opposite ends in apertures formed near the bottoms in both housings. One spring assembly 26 is interconnected between the main pivot pin 32 and the cam disk wing 24a, and the other spring assembly 27 is similarly interconnected between the main pivot pin 32 and the crank disk wing 25a. Each spring assembly 26, 27 includes a spring housing 26a, 27a in which a coil compression spring 27b (shown only for spring housing 27) is contained, and has a spring link 26c, 27c coupled to the compression spring 27b and protruding out an opening in the top of each spring housing. A groove 26e, 27e into which the main pivot pin 32 is received is formed in the bottom of each spring housing 26a, 27a. The spring links 26c, 27c are configured to contain individual pivot pins 26d, 27d, respectively, for interconnection in grooves formed in the free ends of the cam disk wing 24a and the crank disk wing 25a, respectively. The compression springs 26b, 27b tend to bias the cam disk 24 and crank disk 25, respectively, toward one or the other of their maximum rotational states, and each spring-to-disk assembly provides an over-center snap action during rotation between these states of engagement or disengagement of the split-nut pair 22, 23 with the lead screw 15a.

FIG. 5 is a schematic view taken along the axis of the lead screw 15a and illustrates, as an assembly, the aforedescribed interconnection of the cam and crank disks 24, 25 and the spring assemblies 26, 27 between the main pivot pin 32 and the individual pivot pins 26d, 27d. In FIG. 5, both the cam disk 24 and the crank disk 25 are biased by their respective spring assemblies 26, 27 over center in the clockwise direction, with the crank arm 17 in the closed position, grasping the thumbrest 11c, and the split-nut pair 22, 23 engaged with the lead screw 15a. The thumbrest 11c is shown securely captured between the crank arm 17 and a rub strip 33 affixed along the adjacent side wall 12e of the main pump housing 10.

With reference to FIGS. 2 and 5, the split-nut pair 22, 23 are shown abutting so that the generally semi-circular threaded portions of each nut register to form a threaded bore engaging the lead screw 15a as if the split-nut pair were a solid threaded nut. Thus, normal and acceptable thread fit engagement is achieved, radially balanced about the lead screw 15a. The semi-circular threaded portions are chamfered slightly at the abutting faces of the split-nut pair 22, 23 to provide full clearance around the lead screw 15a when the split nuts are disengaged.

Operation of the traveler mechanism 19 will now be explained with reference to FIGS. 6a-6h, which illustrate in order the interaction of the various components as the crank arm 17 is manually rotated counterclockwise from its fully opened position through the full angular extent of its movement and then back again. FIGS. 6a-6h are essentially enlarged views similar to FIG. 5, but fragmented to show only the outlines of the cam disk 24 and the crank disk 25. In addition, the split-nut pair 22, 23 and pins 22a, 23a, the cam grooves 24b, 24c and the key 24k of the cam disk 24, and the keyway 25b of the crank disk 25, are superimposed over one another in these views. The mechanical stops 20e, 20f, 21c, 21d of both the front housing 20 and the rear housing 21 have also been included to aid in orientation, it being appreciated that the mechanical stops of both housings precisely overlay one another in these views. In the description of the operation that follows, reference will be made to FIG. 5 for the purpose of describing the angular position of the crank arm 17 for each of the views.

In FIG. 6a the crank arm 17 is in its fully opened position, rotated to the maximum clockwise extent (i.e., at 60° in FIG. 5), so that a syringe can be installed in the pump 10 and the crank arm 17 can manually be moved along the traveler rod 15 into alignment with the thumbrest 11c on the syringe plunger 11b. Both the crank disk 25 and the cam disk 24 are correspondingly rotated to their maximum clockwise extent, each having its wing 25a, 24a abutting their respective mechanical stops 21d, 20e, and being biased to that state by the spring assemblies 27, 26, which are over or past center to the left in the drawing. The split-nut pair 22, 23, under the control of the cam grooves 24b, 24c in the cam disk 24, are disengaged with the lead screw 15a and moved radially outward in the slide groove to the maximum extent. The split-nut pins 22a, 23a are in the previously described disengagement-locking portions (see FIG. 4a) of the cam grooves 24b, 24c formed for locking the split-nut pair 23, 22 in the fully disengaged position. It should also be noted that the cam disk key 24k is in an intermediate position within the crank disk keyway 25b with 20° of available relative rotation to the left of the key in the drawing and 10° of available rotation to the right.

Referring now to FIG. 6b, the crank arm 17 has been rotated 20° counterclockwise towards the closed position, or in other words so that the centerline of the crank arm is at 40° on the scale shown in FIG. 5. The crank disk 25 likewise has rotated 20° in the counterclockwise direction, but due to the relationship between the key 24k and the keyway 25b, this has not resulted in any movement of the cam disk 24 or, therefore, the split-nut pair 22, 23. In other words, the 20° of relative rotation to the left of the key 24k in FIG. 6a has been consumed by this counterclockwise crank arm rotation, and the keyway 25b is just now beginning to engage the key 24k. There is now 30° of available counterclockwise cam disk rotation relative to the crank disk.

As shown in FIG. 6c, an additional 15° of counterclockwise rotation of the crank arm 17 (or to the 25° mark on the scale of FIG. 5) brings the crank disk 25 and its associated spring assembly 27 to the on-center position. At this point, the cam disk 24 is being driven by the crank disk 25 and thus has also rotated 15° in the counterclockwise direction. The split-nut pair 22, 23 each have moved radially inwardly towards the lead screw 15a a slight amount, however, most of the rotation of the cam disk 24 to this point has been devoted primarily to bringing the split-nut pins 22a, 23a (see FIG. 4a) out of the disengagement-locking portions of the cam grooves 24b, 24c.

Although not shown in the figures, it will be noted that further counterclockwise rotation of the crank arm 17 brings the crank disk 25 over center to the right in the drawings, so that thereafter the crank disk tends to be biased by its spring assembly 27 towards the fully closed position of the crank arm 17. Of course, rotation of the crank disk 25 will be resisted by the cam disk 24 and its associated spring assembly 26, until the crank disk has rotated at least 20° in the counterclockwise direction past the on center position to bring the cam disk over center. As the cam disk 24 approaches and then passes the on-center position, the combined effects of spring biasing of both the cam disk and the crank disk 25 will be such as to automatically drive both towards the fully closed positions.

Continued counterclockwise rotation of the crank arm 17 (FIG. 5), brings it into engagement with the thumbrest 11c of the syringe plunger 11b, assuming that the crank arm and the thumbrest are properly aligned. In FIG. 6d, the center line of the syringe plunger is as shown in FIG. 5, at the 0° mark on the angular scale. In accordance with the invention, the cam disk 24 is no longer being driven by the crank disk 25, but is instead continuing to rotate in the counterclockwise direction due solely to the biasing effects of its spring assembly 26. In this regard, it will be noted in FIG. 6d that the cam disk 24 has rotated relative to the crank disk 25 such that the key 24k and the keyway 25b are no longer engaged, the cam disk 24 having consumed 10° of the previously available 30° of relative counterclockwise rotation.

FIG. 6d also illustrates a condition in which the split-nut pair 22, 23 have moved radially inwardly towards the lead screw 15a, but have not fully engaged because the threads of the split-nut pair are not aligned with the threads of the lead screw 15a. As frequently occurs, the thread crests of the split-nut pair are hung up on the thread crests of the lead screw, full engagement between the threads will not be possible until the lead screw 15a is rotated slightly by the syringe pump motor.

Because the crests of threads in general are relatively weak, those of ordinary skill will appreciate that in the condition represented, there would be a possibility of damaging the threads of the split-nuts 22, 23 and the lead screw 15a if any significant force were applied to the split nuts in an attempt to complete engagement.

With the mechanical engagement and drive system of the present invention, however, this does not occur because the spring assembly 26 of the cam disk 24, which is the only element exerting force on the cam disk, is only 15° over center to the right, so that minimal inwardly-directed force is being exerted on the split-nut pair 22, 23, through the cam grooves 24b, 24c in the cam disk 24.

Moreover, as previously explained in connection with FIG. 4a, the split-nut pin 23b engages the second segment 24h of the cam groove 24b along the engagement path I so as to reduce the collision force of the split-nut threads with the lead screw threads for further protection against damage and therefore preventing premature thread wear.

Slight rotation of the lead screw 15a permits full engagement of the split-nut pair 22, 23 through the biasing of the spring assembly 26 on the cam disk 24. Thus, in response to such lead screw rotation, as shown in FIG. 6e, the cam disk key 24k has consumed the remaining 20° in the keyway 25b available for counterclockwise rotation of the cam disk 24 relative to the crank disk 25, bringing the cam disk 35° over center to the right. This rotation of the cam disk 24 brings the split-nut pins 22a, 23a into the engagement-locking portions of the cam grooves, which serve to lock the split-nut pair 22, 23 in engagement with the lead screw 15a. The cam disk spring assembly 26 now holds the cam disk wing 24a against the mechanical stop 20f, assuring that the split-nut pair 22, 23 will be held in engagement with the lead screw 15a and the crank arm 17 will travel forward along the traveler rod 15 as the lead screw 15a rotates, to result in a pump stroke being applied to the syringe 11.

Of course, in those cases in which the respective threads of the split-nut pair 22, 23 and the lead screw 15a happen to be aligned as the crank arm 17 is rotated into engagement with the thumbrest 11c on the syringe plunger 11b, the relative positions of the components represented by FIG. 6d will be transitory and the cam disk 24 will continue to rotate directly to the state represented by FIG. 6e.

FIG. 6f represents a condition in which the crank arm 17 has not grasped the thumbrest 11c, but has instead rotated fully into the contact with the rub strip 33 on the adjacent sidewall 12e. This occurs under conditions where the syringe 11 is entirely absent from the apparatus, the crank arm 17 is misaligned behind or rearwardly of the thumbrest 11c, or an improperly sized syringe has been installed, such syringe having an undersized thumbrest. The relationship between the key 24k and the keyway 25b permits the crank disk 25 to regain 10° of counterclockwise rotation relative to the cam disk 24, to allow the crank arm 17 to rotate past its 0° position into contact with the rub strip 33. As shown in FIG. 6f, this extra 10° of rotation of the crank disk 25 brings it into phase with the cam disk 24, with the wings of each abutting their respective mechanical stops 21c, 20f on their respective housings 21, 20.

It should be appreciated from FIGS. 6a–6f that the mechanical stop 21c for the crank disk wing 25a, together with the relative play between the key 24k and the keyway 25b, combine to help protect the split nut-pair 22, 23 and the lead screw 15a against damage even as a result of overly vigorous operation of the crank arm 17 by the user during the engagement process. As previously mentioned, in normal operation once the cam disk 24 is driven over center by the crank disk 25, the cam disk disengages the crank disk 25 and tends to continue rotating solely as a result of its own spring assembly 26. If the crank arm 17 is very sharply rotated towards the closed position, it is theoretically possible such disengagement of the cam disk 24 from the crank disk 25 will not occur as soon as the cam disk passes center. Even under the worst circumstances, however, the cam disk 24 will disengage when it is no more than 15° over center, because the crank disk 25 itself would be a maximum 35° over center, leading the cam disk by 20° at this point, and could rotate no further because of the mechanical stop 21c (i.e., assuming the crank arm 17 contacted the rub strip 33, which incidentally also serves as a stop). Since this worst-case disengagement of the cam disk 24 from the crank disk 25 coincides with the earliest possible contact between the split nut-pair 22, 23 and the lead screw 15a at their respective thread crests (see FIG. 6d), the user cannot exert undue engagement forces on the threads in this manner.

Turning now to the operation of the traveler mechanism 19 during the process of rotating the crank arm 17 towards the opened position, it will be appreciated by reference to FIG. 6e, that the crank disk 25 leads the cam disk 24 in the clockwise direction over the initial portion of clockwise rotation because of the relationship between the key 24k and the keyway 25b. This lead phase amounts to 10° of clockwise rotation. Thus, it will be apparent that the crank disk 25 will pass its on-center position 10° ahead of the cam disk 24.

The paths that the split-nut pins 22a, 23a follow within the cam grooves 24c, 24b during clockwise rotation are such that the spring-to-cam disk system must rotate about 10° past its on-center position before there is any outward radial movement of the split-nut pair 22, 23 for disengaging the lead screw 15a. This may be seen in FIG. 6g, where it is apparent that the split-nut pins 22a, 23a thus far have traced a path in the groove defined as a pure arc relative to the center of the disk 24 so that no radial movement of the split-nut pair 22, 23 has occurred.

The condition of the mechanism shown in FIG. 6g is transitory and has been included to illustrate the foregoing point. At the position of rotation of the cam disk 24 shown in FIG. 6g, the split-nut pins 22a, 23a are just engaging steep ramp portions 24j (see FIG. 4a) of the cam grooves 24b, 24c which will tend to drive the split-nut pair 22, 23 very rapidly in the outward radial direction for disengagement of the lead screw 15a. The steep ramp portions 24j (see FIG. 4a) leads directly back to the disengagement-locking portion 24f of the cam grooves 24b, 24c provided for locking the split-nut pair 22, 23 in the fully disengaged position.

Significantly, in the transitory state shown in FIG. 6g, the cam disk 25 is over center so that split-nut pair disengagement has become automatic regardless of whether the user continues to rotate the crank arm 17 to its fully opened position. In this regard, it will be noted that the cam disk 24 is 10° over center to the left and 25° away from the left most mechanical stop 20f, and that there is 25° of available clockwise rotation of the cam disk key 24k relative to the crank disk keyway 25b. This is also apparent by comparing FIG. 6g to FIG. 6b.

It is thus impossible for the user, by rotating and holding the crank arm 17 in a partially opened position, to hold the split nut-pair 22, 23 in a condition of only partial disengagement with the lead screw 15a. The split nut-pair 22, 23 either are fully engaged with the lead screw 15a or rapidly disengage it completely so that no damaging thread scraping can occur during manual repositioning of the crank arm 17.

FIG. 6h corresponds to FIG. 6a and has been included to illustrate that the various components resume their original positions upon rotation of the crank arm 17 to the fully opened position.

In a further aspect of the invention, the mechanical engagement and disengagement system has been designed so that the syringe 11 can be installed in the infusion pump 10 without first attempting to align the crank arm 17 with the thumbrest 11c on the syringe plunger 11b. In this regard, it will be appreciated by viewing FIGS. 1 and 7 that when the crank arm 17 is in the fully opened position, there is sufficient clearance in the space above it to receive the syringe plunger 11b due to the fact that the crank arm rotates out of the way. As previously described, the crank arm 17 is, in fact, biased or "locked" to the opened position due to the biasing force of the crank disk spring assembly 27.

Referring now to FIG. 8, wherein the crank arm 17 is shown schematically in cross-section, the crank arm is provided with a bevelled edge 17a permitting installation of the syringe regardless of the linear position of the crank arm relative to the thumbrest 11c at the time of installation. More specifically, if the crank arm 17 happens to be forward, or to the left in FIG. 8, of the thumbrest 11c the crank arm can be manually moved rearwardly, or to the right in FIG. 8, and as the bevelled edge 17a on the crank arm contacts the plunger side of the thumbrest it will cam the plunger 11b to be lifted over the crank arm. After the crank arm passes by, the syringe plunger 11b then will typically return to its original position by force of gravity, and the crank arm is then moved forwardly into proper alignment with the end of the thumbrest. Automatic alignment is achieved due to the fact that the margin of the pushing surface 17b of the crank arm 17 most nearly adjacent the thumbrest 11c has a slight interference fit with the thumbrest when approaching it from the rear (or right, in FIG. 8). Thus, alignment of the crank arm 17 will be indexed when the margin of the syringe plunger pushing surface 17b contacts the thumbrest 11c. At this point, the crank arm 17 is in position to be rotated inwardly and upwardly to grasp the thumbrest 11c in an anti-syphon groove 17c formed in the crank arm. Of course, if the crank arm 17 is initially rearward (or to the right) of the thumbrest 11c at the time of syringe installation, the crank arm is simply slid forward until properly indexed with the thumbrest.

As best shown by the enlarged framentary end view in FIG. 2a, proper engagement of the crank arm 17 with the thumbrest 11c is electro-optically monitored by the optical mechanism 28 which includes a combined light source and photoelectric sensor assembly 28a affixed to the outer surface of the rear housing 21. A torsional spring 28b is coiled about a first post 21f that extends axially outward from one of the holes in the rear housing 21 used to fasten it to the front housing 20 (FIG. 2), and one extended portion 28b of the spring is directed across the top of the rear housing and fastens to a second post 21g axially protruding from the other mounting hole. An opposite extended portion 28b" of the spring is directed downwardly from the first post 21f and carries an opaque flag 28c mounted normal to the spring wire. A collar 18a, on which a cam lobe 18a' is formed, is fixed on the hollow crank shaft 18 immediately adjacent the outer surface of the rear housing 21, as by a pin.

As shown in FIG. 2, when the crank arm 17 is fully engaged with the thumbrest 11c, the cam lobe 18a' cams the downwardly extending spring portion 28b" outwardly so that the opaque flag 28c does not interrupt the reference light beam between the light source and photoelectric sensor 28a. In any other angular position of the crank arm 17, the cam lobe 18a' is rotated out of engagement with the spring wire portion 28b" so that its natural spring bias moves the opaque flag 28c inwardly to interrupt the reference light beam. A corresponding electrical signal is generated to indicate the angular state of the crank arm 17 to the control system of the infusion pump 10. The control system in turn can use this signal as one of many enabling signals for pump operation and to trigger appropriate alarms or otherwise indicate the state of the crank arm to medical personnel using the pump.

The mechanical engagement and disengagement system of the present invention satisfies a long existing need for improved, relatively simple, economical and reliable mechanisms for screw drive and syringe pump engagement and disengagement. The system tends to ensure against undue wear and damage to the threads of both lead screws and traveler mechanisms, and provides simplified syringe installation and plunger mover alignment.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. The combination comprising:
   a lead screw;
   traveler means actuable between states of threaded engagement and disengagement with said lead screw, said traveler means including biasing means for biasing said traveler means in said state of engagement and in said state of disengagement, said biasing means producing an over-center action during movement of said traveler means between said state of engagement and said state of disengagement;
   actuating means, selectively operable, for actuating said traveler means; and
   means for coupling said actuating means to said traveler means to allow limited relative movement between said actuating means and said traveler means, such that said traveler means moves to said state of engagement independently of said actuating means after said biasing means has moved over center, and further such that said traveler means begins to engage said lead screw in moving to said state of engagement only after said biasing means has moved over center.

2. A combination as set forth in claim 1, and further including:
   means for limiting collision forces between said traveler means and said lead screw as said traveler means moves to said state of engagement.

3. The combination comprising:
   a lead screw;
   traveler means actuable between states of threaded engagement and disengagement with said lead screw, said traveler means including biasing means for biasing said traveler means in said state of engagement and in said state of disengagement, said biasing means producing an over-center action during movement of said traveler means between said state of engagement and said state of disengagement;
   actuating means, selectively operable, for actuating said traveler means; and
   means for coupling said actuating means to said traveler means to allow limited relative movement between said actuating means and said traveler means, such that said traveler means moves to said state of disengagement independently of said actuating means after said biasing means has moved over center, and further such that said traveler means begins to disengage said lead screw in moving to said state of disengagement only after said biasing means has moved over center.

4. A combination as set forth in claim 3, and further including:
   means for rapidly moving said traveler means to said state of disengagement after said biasing means has moved over center.

5. The combination comprising:
   a lead screw;
   traveler means actuable between states of threaded engagement and disengagement with said lead screw, said traveler means including biasing means for biasing said traveler means in said state of engagement and in said state of disengagement, said biasing means producing an over-center action during movement of said traveler means between said state of engagement and said state of disengagement;
   actuating means, selectively operable, for actuating said traveler means; and
   means for coupling said actuating means to said traveler means to allow limited relative movement between said actuating means and said traveler means, such that said traveler means moves between said state of engagement and said state of disengagement independently of said actuating means after said biasing means has moved over center, and further such that said traveler means begins to engage said lead screw in moving to state of engagement, and begins to disengage said lead screw in moving to said state of disengagement, only after said biasing means has moved over center.

6. A combination as set forth in claim 5, and further including:
   means for limiting collision forces between said traveler means and said lead screw as said traveler means moves to said state of engagement.

7. A combination as set forth in claim 5, and further including:
   limit means for limiting the range of operation of said actuating means.

8. A combination as set forth in claim 5, and further including:
   means for rapidly moving said traveler means to said state of disengagement after said biasing means has moved over center.

9. The combination comprising:
   a lead screw;
   a pair of split nuts disposed on opposite sides of said lead screw and mounted for movement into and out of engagement with said lead screw;
   rotary cam means for controlling the movement of said split nuts;

actuating means, selectively operable, for actuating said rotary cam means;

first biasing means for biasing said rotary cam means in either one of opposite rotational states, said first biasing means producing an over-center action with said rotary cam means during rotation between said opposite rotational states; and means for coupling said actuating means to said rotary cam means to allow limited relative movement between said actuating means and said rotary cam means, such that said rotary cam means controls movement of said split nuts independently of said actuating means after said rotary cam means has travelled over center, and further such that rotation of said rotary cam means in a first direction between said opposite rotational states causes movement of said split nuts into engagement with said lead screw only after said rotary cam means has travelled over center.

10. A combination as set forth in claim 9, wherein said split nuts and said rotary cam means are freely moveable along said lead screw as a unit when said split nuts are disengaged from said lead screw.

11. A combination as set forth in claim 9, wherein rotation of said rotary cam means in a second direction between said opposite rotational states causes movement of said split nuts out of engagement with said lead screw only after said rotary cam means has travelled over center.

12. A combination as set forth in claim 9, and further including:
limit means for limiting the range of operation of said actuating means.

13. A combination as set forth in claim 9, wherein said means for actuating said rotary cam means comprises rotary crank means for rotating said rotary cam means.

14. A combination as set forth in claim 13, and further including:
second biasing means for biasing said rotary crank means towards either one of opposite rotational states, said second biasing means producing an over-center action with said rotary crank means during rotation between said opposite rotational states.

15. The combination comprising:
a lead screw;
a plurality of threaded members mounted for movement into and out of engagement with said lead screw;
control means for controlling movement of said threaded members;
first biasing means for biasing said control means in a disengaged state when said threaded members are fully disengaged from said lead screw, and in an engaged state when said threaded members are fully engaged to said lead screw, said first biasing means producing an over-center action with said control means during movement between said engaged state and said disengaged state; and
means for coupling said actuating means to said control means to allow limited relative movement between said actuating means and said control means, such that said control means controls movement of said threaded members independently of said actuating means after said control means has travelled over center, and further such that said threaded members begin to engage said lead screw only after said control means has travelled over center towards said engaged state.

16. A combination as set forth in claim 15, wherein said threaded members, said control means, said first biasing means and said actuating means are freely moveable along said lead screw as a unit when said split nuts are disengaged from said lead screw.

17. A combination as set forth in claim 15, wherein said control means includes means for limiting collision forces between said threaded members and said lead screw upon engagement.

18. A combination as set forth in claim 15, wherein said control means comprises a rotary cam and said actuating means comprises a rotary crank.

19. A combination as set forth in claim 15, wherein said threaded members begin to disengage said lead screw only after said control means has travelled over center towards said disengaged state.

20. A combination as set forth in claim 19, wherein said control means includes means for rapidly disengaging said threaded members from said lead screw after said control means has travelled over center.

21. A combination as set forth in claim 19, wherein said control means comprises a rotary cam and said actuating means comprises a rotary crank.

22. In a syringe pump for delivering a pump stroke to a syringe having a syringe plunger, the combination comprising:
means for releasably holding the syringe in the syringe pump;
plunger mover means mounted for rotation between a first position and a second position, said plunger mover means in said first position disposed in axial alignment with the free end of the plunger, and said plunger mover means in said second position providing clearance to freely install the syringe in the syringe pump regardless of the linear position of said plunger mover means relative to the free end of the syringe plunger;
means for imparting relative linear motion between said plunger mover means and the syringe along the axis of the syringe plunger; and
index means, carried by said plunger mover means, for indexing said plunger mover means, when in said second position, in proper linear alignment for full engagement with the free end of the syringe plunger when said plunger mover means is rotated to said first position, said index means indexing said plunger mover means when in said second position by partial engagement of said plunger mover means with the free end of the syringe plunger.

23. A combination as set forth in claim 22, and further including:
means, connected to said plunger mover means, for releasably biasing said plunger mover means in said first position.

24. A combination as set forth in claim 22, and further including:
means, connected to said plunger mover means, for releasably biasing said plunger mover means in said second position.

25. A combination as set forth in claim 22, and further including:
biasing means for biasing said plunger mover means in said first position and in said second position, said biasing means producing an over-center action with said plunger mover means during rotation between said first position and said second position.

26. A combination as set forth in claim 25, wherein said plunger mover means comprises an arm.

27. A combination as set forth in claim 22, and further including:
  sensing means for sensing if said plunger mover means is in said first position.

28. A combination as set forth in claim 22, wherein said syringe pump further includes means for disengaging said means for imparting relative linear motion such that said plunger mover means is capable of free linear motion relative to the syringe.

29. A combination as set forth in claim 28, wherein said plunger mover means comprises an arm having a pushing surface adapted for engagement with the free end of the plunger when said plunger mover means is in said first position, and wherein said index means comprises a portion of said pushing surface.

30. A combination as set forth in claim 28, wherein said index means indexes in only one direction of free linear motion between said plunger mover means and the free end of the plunger.

31. A combination as set forth in claim 30, wherein said index means further includes camming means for camming said plunger mover means past the free end of the plunger in the opposite direction of free linear motion.

32. A combination as set forth in claim 31, wherein said plunger mover means comprises an arm having a pushing surface adapted for engagement with the free end of the plunger when said plunger mover means is in said first position, wherein said indexing means comprises a portion of said pushing surface, and wherein said camming means comprises a camming surface on said arm.

33. In a syringe pump for delivering a pump stroke to a syringe having a syringe plunger, the combination comprising:
  a lead screw;
  a pair of split nuts disposed on opposite sides of said lead screw and mounted for movement into and out of engagement with said lead screw;
  control means for controlling the movement of said split nuts; and
  plunger mover means, coupled to said control means, for pushing against the free end of the syringe plunger,
  said plunger mover means being mounted for selective rotation between a first position, in which said plunger mover means engages the free end of the plunger and actuates said control means to an engaged state in which said split nuts are engaged to said lead screw, and a second position, in which the plunger mover means is disengaged from the free end of the plunger and actuates said control means to a disengaged state in which said split nuts are disengaged from said lead screw.

34. A combination as set forth in claim 33, wherein said split nuts, said control means and said plunger mover means are freely moveable along said lead screw as a unit when said split nuts are disengaged from said lead screw.

35. A combination as set forth in claim 34, and further including:
  first biasing means for biasing said control means in said engaged state and in said disengaged state, said first biasing means producing an over-center action with said cam means during movement between said engaged state and said disengaged state.

36. A combination as set forth in claim 35, wherein movement of said control means from said disengaged state towards said engaged state causes movement of said split nuts into engagement with said lead screw only after said control means has travelled over center, and further including:
  means for coupling said plunger mover means to said control means to allow limited relative movement between said plunger mover means and said control means, such that said control means controls movement of said split nuts into engagement with said lead screw independently of said plunger mover means after said control means has travelled over center, said control means including means for limiting collision forces between said split nuts and said lead screw upon engagement.

37. A combination as set forth in claim 35, wherein movement of said control means from said engaged state towards said disengaged state causes movement of said split nuts out of engagement with said lead screw only after said control means has travelled over center, and further including:
  means for coupling said plunger mover means to said control means to allow limited relative movement between said plunger mover means and said control means, such that said control means controls movement of said split nuts out of engagement with said lead screw independently of said plunger mover means after said control means has travelled over center, said control means including means for rapidly disengaging said split nuts from said lead screw after said control means has travelled over center.

38. A combination as set forth in claim 35, wherein said control means comprises a cam and said plunger mover means comprises a crank arm.

39. A combination as set forth in claim 35, and further including:
  sensing means for sensing if said plunger mover means is in said first position.

40. A combination as set forth in claim 35, and further including:
  second biasing means for releasably biasing said plunger mover means in said first position and in said second position.

41. In a syringe pump for delivering a pump stroke to a syringe having a syringe plunger, the combination comprising:
  a lead screw;
  traveler means actuable between states of threaded engagement and disengagement with said lead screw, said traveler means including a plurality of threaded members disposed about said lead screw such that in said state of engagement the forces exerted by said threaded members on said lead screw are substantially balanced relative to one another; and
  plunger mover means, coupled to said traveler means, for pushing against the free end of the syringe plunger,
  said plunger mover means being mounted for selective rotation between a first position, in which said plunger mover means engages the free end of the plunger and actuates said traveler means to said state of engagement with said lead screw, and a second position, in which said plunger mover means is disengaged from the free end of the plunger and actuates said traveler means to said state of disengagement with said lead screw.

42. A combination as set forth in claim 41, wherein said traveler means and said plunger mover means are freely moveable along said lead screw as a unit when said plunger mover means is in said second position and said traveler means is in said state of disengagement.

43. A combination as set forth in claim 42, wherein said traveler means includes first biasing means for releasably biasing said traveler means in said state of engagement and in said state of disengagement.

44. A combination as set forth in claim 43, wherein said first biasing means produces an over-center action during actuation of said traveler means between said state of engagement and said state of disengagement.

45. A combination as set forth in claim 44, and further including:
second biasing means for releasably biasing said plunger mover means in said first position and in said second position.

46. A combination as set forth in claim 45, wherein said second biasing means produces an over-center action during rotation of said plunger mover means between said first position and said second position.

47. A combination as set forth in claim 46, wherein said traveler means is actuated into said state of engagement only after said first biasing means has travelled over center.

48. A combination as set forth in claim 46, wherein said traveler means is actuated into said state of disengagement only after said first biasing means has travelled over center.

49. A combination as set forth in claim 46, and further including:
means for coupling said plunger mover means to said traveler means to allow limited relative movement between said plunger mover means and said traveler means, such that said traveler means moves between said state of engagement and said state of disengagement independently of said plunger mover means after said first biasing means has travelled over center.

50. A combination as set forth in claim 49, and further including:
means for limiting collision forces between said traveler means and said lead screw as said traveler means moves to said state of engagement; and
means for rapidly moving said traveler means to said state of disengagement after said first biasing means has moved over center.

51. A combination as set forth in claim 41, and further including:
sensing means for sensing if said plunger mover means is in said first position.

* * * * *